United States Patent
Griffin

(10) Patent No.: US 8,282,676 B2
(45) Date of Patent: Oct. 9, 2012

(54) TAPERED THREAD ROOT TRANSITION ON CORTICAL BONE FASTENER

(76) Inventor: T. Hall Griffin, Longview, TX (US)

(*) Notice: Subject to any disclaimer, the term of this patent is extended or adjusted under 35 U.S.C. 154(b) by 322 days.

(21) Appl. No.: 12/455,226

(22) Filed: May 28, 2009

(65) Prior Publication Data

US 2010/0305622 A1 Dec. 2, 2010

(51) Int. Cl.
*A61B 17/04* (2006.01)
(52) U.S. Cl. .......... 606/309; 606/301; 606/316
(58) Field of Classification Search .......... 606/300–301, 606/315–317; 623/13.11, 13.14, 16.11
See application file for complete search history.

(56) References Cited

U.S. PATENT DOCUMENTS

| | | | |
|---|---|---|---|
| 5,242,447 A | 9/1993 | Borzone | |
| 5,259,398 A | 11/1993 | Vrespa | |
| 5,593,410 A | 1/1997 | Vrespa | |
| 5,665,087 A | 9/1997 | Huebner | |
| 5,720,766 A | 2/1998 | Zang | |
| 5,961,524 A | 10/1999 | Crombie | |
| 6,375,657 B1 | 4/2002 | Doubler et al. | |
| 6,565,573 B1 | 5/2003 | Ferrante et al. | |
| 6,949,100 B1 | 9/2005 | Venturini | |
| 6,953,463 B2 | 10/2005 | West, Jr. | |
| 7,001,389 B1 | 2/2006 | Navarro et al. | |
| 7,198,488 B2 | 4/2007 | Lang et al. | |
| 2001/0047175 A1 | 11/2001 | Doubler et al. | |
| 2002/0045897 A1 | 4/2002 | Dixon et al. | |
| 2003/0158555 A1* | 8/2003 | Sanders et al. ............ | 606/73 |
| 2004/0172033 A1 | 9/2004 | Bonutti | |
| 2005/0171544 A1* | 8/2005 | Falkner ............ | 606/69 |
| 2005/0250074 A1* | 11/2005 | Lang et al. ............ | 433/174 |
| 2006/0106389 A1* | 5/2006 | Reber et al. ............ | 606/72 |
| 2006/0116686 A1 | 6/2006 | Crozet | |
| 2007/0053765 A1 | 3/2007 | Warnick et al. | |

FOREIGN PATENT DOCUMENTS

KR 20-0380861 Y1 4/2005

OTHER PUBLICATIONS

International Search Report and Written Opinion of the International Searching Authority from PCT/US2010/035710 mailed Dec. 29, 2010.
Timothy L. Biliouris et al.: "The effect of radial preload on the implant-bone interface: a cadaveric study"; Journal of Orthopaedic Trauma, vol. 4, No. 3, pp. 323-332; c 1989.
C. Hyldahl et al:"Induction and prevention of pin loosening in external fixation: an in vivo study on sheep tibiae"; Journ. of Orth. Trauma, vol. 5, No. 4, pp. 485-492; c 1991.

* cited by examiner

*Primary Examiner* — Thomas Barrett
*Assistant Examiner* — Melissa A Golob
(74) *Attorney, Agent, or Firm* — Zeman-Mullen & Ford, LLP

(57) ABSTRACT

An orthopedic fastener is disclosed, with a cylindrical shank having pre-selected diameter, the shank also providing adjacent unthreaded and threaded portions. The threaded portion is configured to secure the orthopedic fastener into cortical bone. The shank further has a thread root transition zone providing a tapered thread root profile between the unthreaded and threaded portions. The thread root transition zone is positioned on the shank such that, when the orthopedic fastener is operably secured into a specimen of cortical bone, the thread root transition zone is located outside of the specimen of cortical bone.

20 Claims, 4 Drawing Sheets

TAPERED THREAD ROOT TRANSITION ON CORTICAL BONE FASTENER

RELATED APPLICATIONS

None.

FIELD OF THE INVENTION

This invention relates generally to orthopedic fasteners configured to secure into cortical bone, and more particularly, in a preferred embodiment, to an orthopedic fastener with a tapered thread root transition between threaded and unthreaded portions that is operably located outside the bone.

BACKGROUND OF THE INVENTION

Designs of threaded orthopedic fasteners have historically struggled with a transition from unthreaded to threaded portions. The manufacturing process of cutting a thread on a shank typically leaves an abrupt discontinuity between threaded and unthreaded portions, where the thread root diameter is less than the unthreaded shank diameter. Problems occur when such orthopedic fasteners are secured into bone. When repetitive loads are exerted on the secured fastener (such as are likely to be experienced in exemplary orthopedic procedures such as bone distraction or fracture repair), such fasteners become inherently susceptible to acute and/or fatigue failure at the abrupt threaded/unthreaded transition, since repetitive loads become more focused at the threaded/unthreaded discontinuity when the fastener is held rigidly.

This tendency towards failure is especially pronounced when such orthopedic fasteners are secured into cortical bone. Cortical bone, typically found on the outside of a bone, is harder than cancellous bone, typically found on the inside of a bone. This means that threads on orthopedic fasteners can typically be fastened tighter into cortical bone than cancellous bone. This in turn means that when the fastener is secured into cortical bone, it can be held more rigidly than when secured into cancellous bone, causing repetitive loads on the fastener to become yet more focused at the threaded/unthreaded discontinuity.

The orthopedic fasteners of the present invention are designed and claimed for use in cortical bone. That is not to say that they may not have serviceable applications in certain types of cancellous bone. However, the focus is on cortical bone.

The references in the previous paragraphs to cortical and cancellous bone deserve further discussion. Orthopedic fasteners are typically designed to fasten either cortical bone or cancellous bone. As noted above, cortical bone, typically found on the outside of a bone, is tougher and harder than cancellous bone, which is typically found on the inside of a bone. Cancellous bone has soft and malleable characteristics, making it useful in, for example, bone grafts. In comparison, cortical bone is considerably harder. When over-stressed, cortical bone will typically crack (at the higher stresses), whereas cancellous bone will typically deform and "pack" (at the lower stresses). As a result, these and other differences in the material properties of cortical and cancellous bone compel different thread designs for orthopedic fasteners. For, example, the thread profile provided on some types of cancellous bone fasteners is a thinner and sharper thread, designed to hold an unimpaired thickness of cancellous bone between the threads, thereby reinforcing the security of the fastener as placed in the cancellous bone. In this way, cancellous bone fasteners of this design will secure into the cancellous bone without "packing" or otherwise deforming the malleable cancellous bone between threads. In contrast, thread profiles provided on other types of cancellous bone fasteners are configured to do the opposite. Such designs are configured to intentionally "pack" the surrounding cancellous bone in order to afford better friction grip on the threads.

Published U.S. Patent Application No. 2003/0158555 (Sanders et al.) discloses conventional orthopedic fastener for use in either cortical or cancellous bone, depending on the type of accompanying threads selected, such as has been described in the previous few paragraphs. More specifically, FIG. 1a of Sanders et al. discloses an abrupt discontinuity between unthreaded and threaded portions. As noted above, the abrupt discontinuity is likely to make the fastener increasingly susceptible to repetitive load failure at the discontinuity once the fastener is secured into bone.

Some prior art designs have attempted to overcome the problems with abrupt discontinuities by providing threads whose root diameter is the same as the shank diameter. While serviceable, such designs are not preferable because of the more complicated fastener manufacturing required to provide threads whose root diameter is the same as the shank diameter upon which they are deployed. Some designs of this type are also disadvantageous in that the bending resistance of the shank is diminished by wholesale removal of metal down to a thread root diameter.

Other prior art designs have attempted to overcome the problems with abrupt discontinuities by providing transitional thread roots between unthreaded to threaded portions to smooth out the transition. Typically, such prior art thread root transitions are conical in shape. For example, U.S. Pat. No. 5,242,447 (Borzone) discloses, in FIG. 2, a threaded pin with a tapered thread root over the entire length of the threaded portion. Such an arrangement is considered disadvantageous, in that a specimen of cortical bone receiving the pin must inevitably also receive at least a portion of tapered thread root transition. In such an arrangement, the tapered thread root transition, especially near the unthreaded portion of the pin, is likely to cause unwanted radial stress on the zone of cortical bone immediately surrounding the point of entry of the pin, resulting in almost inevitable damage to the bone during insertion of the pin. Such unwanted radial stress is also likely to lead to cracking of the bone over time, especially in the presence of operational repetitive loading of the pin. Typically this repetitive-load cracking condition begins from radial stress micro-cracks caused by insertion of the pin. The micro-cracks enlarge and degenerate into substantial cracks as repetitive operational loads are placed upon the pin.

U.S. Pat. No. 6,949,100 (Venturini) discloses, in FIGS. 1 and 2, a bone screw with a tapered thread root over the entire length of the threaded portion. Such an arrangement is disadvantageous for the same reasons as discussed immediately above with respect to U.S. Pat. No. 5,242,447 (Borzone). Indeed, one disclosed embodiment in Venturini teaches a conical taper of approximately 2 mm in reduced thread root diameter over the length of the taper. Those of ordinary skill in this art will understand the radial stress exerted on cortical bone by a thread root diameter change of 2 mm to be inoperable on cortical bone, almost inevitably causing cracking of the bone at the point of entry while attempting to secure the pin. Such a thread root diameter change, coupled with the thread shape and profile disclosed by Venturini, are clearly understood by those of ordinary skill in this art to be indicative of a bone screw better suited for fixation in cancellous bone, not cortical bone.

U.S. Patent Application No. 2007/0053765 (Warnick et al.) discloses numerous styles of threads for bone screws, at least one of which (for example, in FIG. 3) provides a tapered thread root transition zone. However, those of ordinary skill in the art will understand that the tapered thread root transition zone disclosed by Warnick et al. is intended to be inserted at least partially into the bone, noting that removal of the tapered root transition from inside the bone is likely to cause re-tightening issues. Additionally, as noted above with respect to Borzone and Venturini, the considerable radial stress exerted on cortical bone at the point of entry of a tapered root transition zone into the bone renders such tapered thread root transitions highly disadvantageous when located inside cortical bone.

U.S. Pat. No. 7,198,488 (Lang et al.) discloses a dental implant suitable for receiving crowns and other false teeth, at least one embodiment of which provides a tapered thread root transition zone. However, those of ordinary skill in this art will understand that the tapered root transition zone disclosed by Lang et al. is intended to be inserted entirely into the bone.

U.S. Pat. No. 5,665,087 (Huebner) discloses, in FIG. 1, a bone screw with a tapered thread root. However, those of ordinary skill in this art will understand that the tapered thread root disclosed by Huebner is intended to be inserted entirely into the bone. Moreover, it will be seen from the disclosure of Huebner that the bone screw is designed for use in cancellous bone.

Therefore, there exists a need for an improved threaded orthopedic fastener whose discontinuity between threaded and unthreaded portions has increased fatigue life performance (i.e., is resistant to repetitive loads) when secured into cortical bone. Other pitfalls encountered by the prior art also should be avoided, such as deploying a tapered thread root transition inside the cortical bone.

SUMMARY OF THE INVENTION

The present invention addresses one or more of the above-described drawbacks of the prior art. One aspect of this invention includes an orthopedic fastener with a cylindrical shank having pre-selected diameter, the shank also providing adjacent unthreaded and threaded portions. In this aspect of the invention, the threaded portion is configured to secure the orthopedic fastener into cortical bone. The shank further has a thread root transition zone providing a tapered thread root profile between the unthreaded and threaded portions. The tapered thread root profile transitions from zero to full thread cut over a predetermined number of thread turns. The thread root transition zone is positioned on the shank such that, when the orthopedic fastener is operably secured into a specimen of cortical bone, the thread root transition zone is located outside said specimen of cortical bone.

It will be understood that in locating the thread root transition zone outside the specimen of cortical bone, the invention is expressly not limited to a location completely outside the bone. For example, without limitation, the thread root transition zone could be located in a zone of cancellous bone or fatty bone marrow (such as is frequently found between two thicknesses of cortical bone) while the fastener is secured into cortical bone.

It is therefore a technical advantage of the invention to provide a tapered thread root transition between unthreaded and threaded portions on an orthopedic fastener, such that when the tapered root transition is located outside cortical bone into which the orthopedic fastener is operably secured, the discontinuation between the unthreaded and threaded portions will be more resistant to failure from repetitive loading.

A further technical advantage of the invention is that the tapered thread root transition is relatively straightforward to manufacture.

A further technical advantage of the invention is that since the tapered thread root transition is advantageously located outside of cortical bone into which the orthopedic fastener may be secured, the taper on the thread root transition does not add any radial stress to the cortical bone immediately around the fastener.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
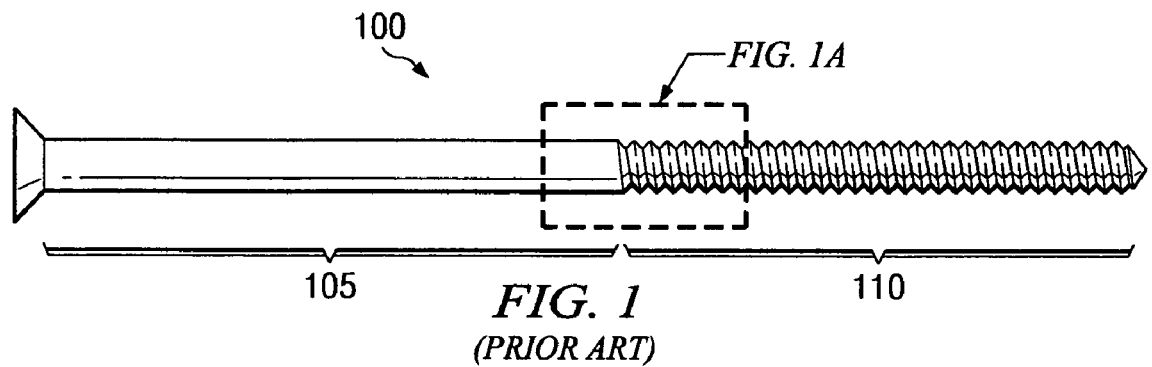
FIGS. 1 and 1A depict a prior art fastener 100 having an abrupt discontinuity 115 between adjacent threaded and unthreaded portions.
Figure 1A:
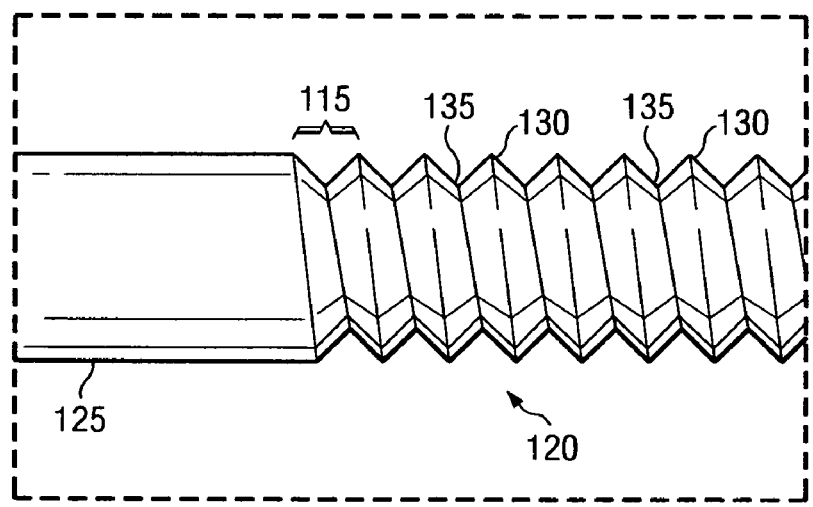

As has been described above more generally with respect to the prior art, FIGS. 1 and 1A depict a prior art fastener 100 with unthreaded portion 105 immediately adjacent to threaded portion 110. FIG. 1A is an enlarged detail view as shown on FIG. 1. As is typical in the prior art, an abrupt discontinuity 115 occurs at the transition from unthreaded portion 105 to threaded portion 110. It will be appreciated that in the typical manufacture of prior art fastener 100, threads 120 are cut on to shank 125 such that thread crests 130 are substantially the same diameter as shank 125, while thread roots 135 have a smaller diameter than the diameter of shank 125. An abrupt change in fastener core diameter thus occurs at discontinuity 115, enhancing the susceptibility of fastener 100 to failure at discontinuity 115 when fastener 100 is subjected to operational loads.

Figures 2, 2A:
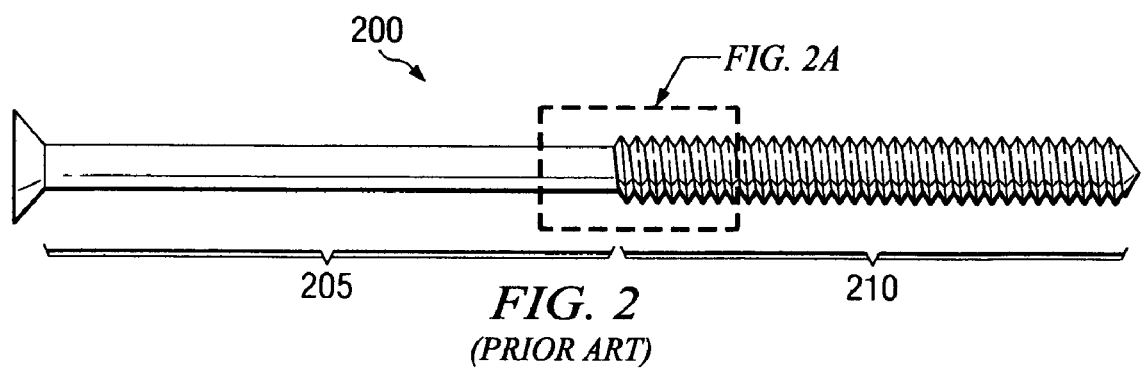
FIGS. 2 and 2A depict a prior art fastener 200 in which an abrupt discontinuity between adjacent threaded and unthreaded portions is avoided by providing thread roots 235 with a diameter substantially the same as the diameter of shank 225.

A further example of the prior art is depicted in FIGS. 2 and 2A. FIG. 2A is an enlarged detail view as shown on FIG. 2. Prior art fastener 200 again provides unthreaded portion 205 immediately adjacent to threaded portion 210. However, in FIGS. 2 and 2A, and in comparison to FIGS. 1 and 1A, threads 220 are provided on shank 225 such that thread roots 235 are substantially the same diameter as shank 225, while thread crests 230 have a larger diameter than the diameter of shank 225. As a result, prior art fastener 200 does not have an abrupt change in fastener core diameter as may be seen on FIG. 1A. However, as described above in more detail in the "Background" section of this disclosure, prior art fasteners of the style depicted in FIGS. 2 and 2A have proven to be disadvantageous, in that wholesale removal of metal on shank 225 down to the diameter of thread roots 235 significantly reduces the operational bending resistance of shank 225, and further significantly increases overall manufacturing costs.

Figure 3:
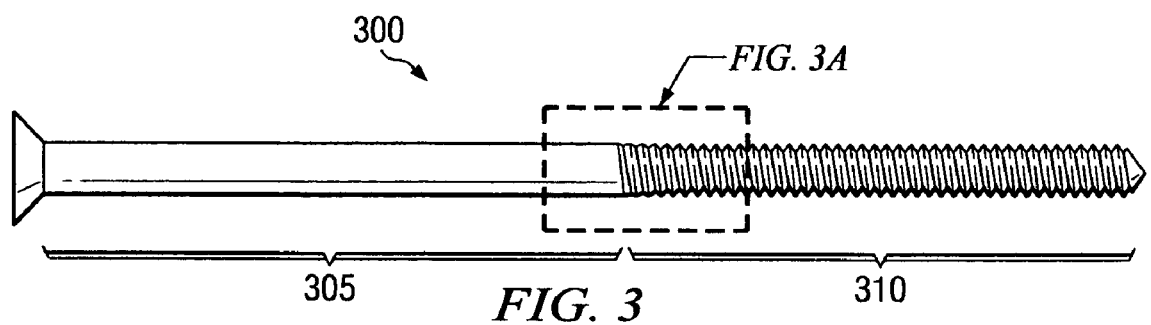
FIGS. 3 and 3A depict a fastener 300 generally in accordance with the present invention, including a thread root transition zone 315.
Figure 3A:
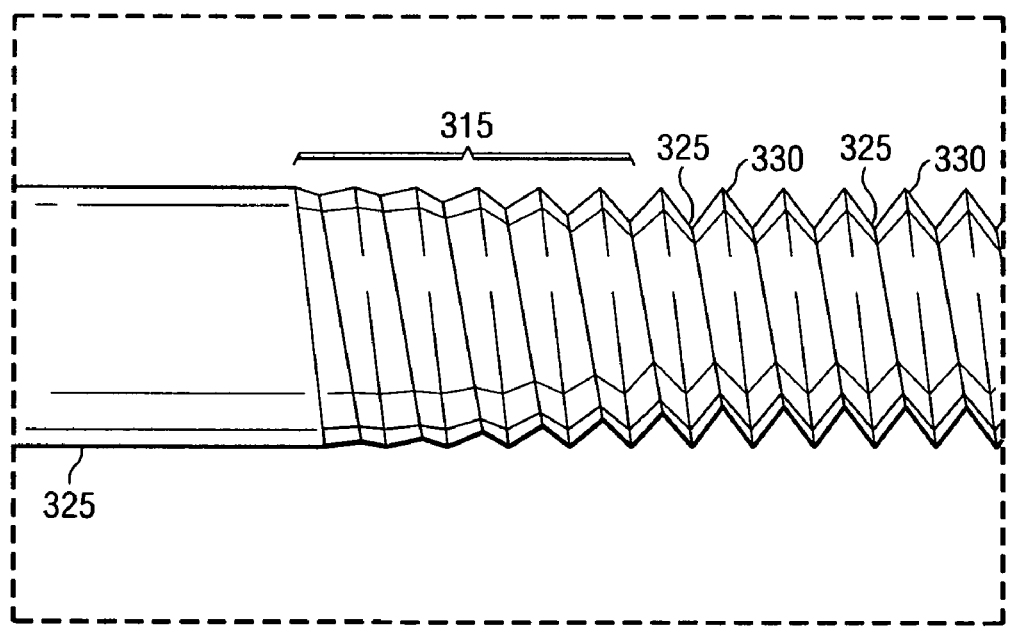

FIGS. 3 and 3A illustrate an exemplary embodiment generally in accordance with the present invention. FIG. 3A is an enlarged detail view as shown on FIG. 3. Fastener 300 provides unthreaded portion 305 adjacent to threaded portion 310. In the illustrated exemplary embodiment, thread crests 330 on threaded portion 310 have a diameter substantially the same as the diameter as shank 325 on unthreaded portion 305. In this way, the disadvantages of prior art fasteners such as described above with reference to FIGS. 2 and 2A are avoided. However, although the exemplary embodiment of FIGS. 3 and 3A illustrates thread crests 330 having a diameter substantially the same as the diameter on shank 325, it will be appreciated that the invention is not limited in this regard. Other embodiments of the invention (not illustrated) may, for example, provide thread crests 330 with a varying diameter along threaded portion 310, or with a uniform thread crest diameter that is different from the diameter of shank 325.

With further reference to FIG. 3A, however, and in distinction to prior art fasteners such as described above with respect to FIG. 1A, a thread root transition zone 315 is provided on fastener 300. In thread root transition zone 315, thread roots 325 are deployed to decrease in diameter in tapered fashion from the diameter of shank 325 to a constant diameter that is less than the diameter of shank 325. In this way, the disadvantages of an abrupt discontinuity between unthreaded and threaded portions are avoided (such as discontinuity 115 as described above with reference to FIGS. 1 and 1A). With further reference to FIG. 3A, it will be clearly seen that thread root transition zone 315 provides a thread cut shape (on FIG. 3A, sn isosceles triangle) formed between each adjacent pair of threads on thread root transition zone 315, where each thread cut shape is defined by an imaginary line between adjacent thread crests and opposing thread slopes running from those adjacent thread crests down to a common thread root. It will be clearly seen on FIG. 3A that thread root transition zone 315 is configured such that for each adjacent pair of threads therein, an angle subtended by the imaginary line and opposing thread slopes increase as thread root transition zone 315 moves from unthreaded to threaded portions of the shank (items 305 and 310 as illustrated on FIG. 3).

Embodiments of the invention have been illustrated and described herein using fixation pins as exemplary orthopedic fasteners. It will be appreciated, however, that the invention is not limited in this regard, and that it may be embodied on any orthopedic fastener, such as, without limitation, pedicle screws, orthopedic nails, bone screws, locking screws, hip screws, or even dental implants.

It will be further appreciated, with further reference to FIG. 3A, that although the exemplary embodiment of thread root transition zone 315 has been illustrated as a conically tapered root, the invention is not limited in this regard. It will be appreciated that the scope of the invention includes other root tapers, such as, for example, a curved taper.

In a preferred embodiment, the thread root transition zone may provides any number in a range from about two (2) to about five (5) thread turns for the tapered thread root profile to transition from zero threaded profile to full threaded profile. It will be appreciated, however, that the invention is not limited in this regard, and that a thread root transition zone providing any number of thread turns to accomplish the transition is within the scope of the invention.

Those of ordinary skill in this art will further appreciate that the invention is not limited to any particular size of orthopedic fastener on which the thread root transition zone may be deployed.

Figure 4A:
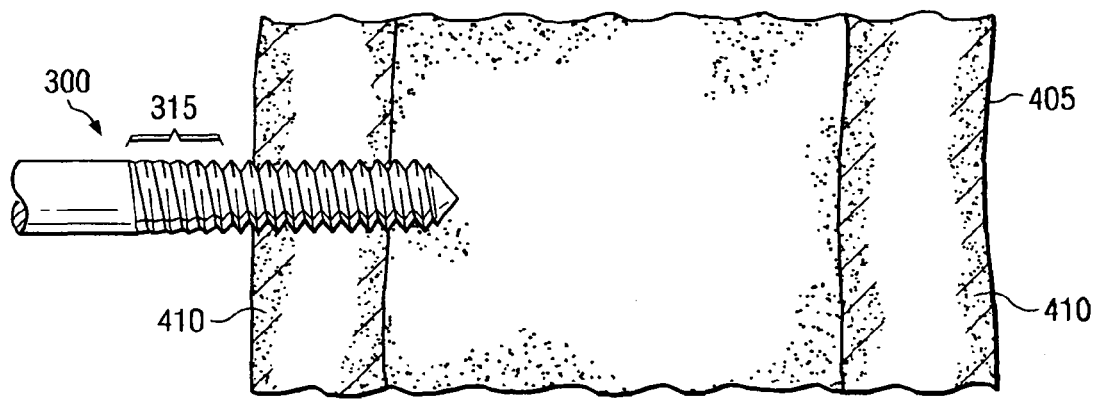
FIG. 4A is a cross-section view of a bone specimen 405, depicting an exemplary deployment of the fastener 300 of FIGS. 3 and 3A operably secured in cortical bone 405, where thread root transition zone 315 is located completely outside the bone.
Figure 4B:
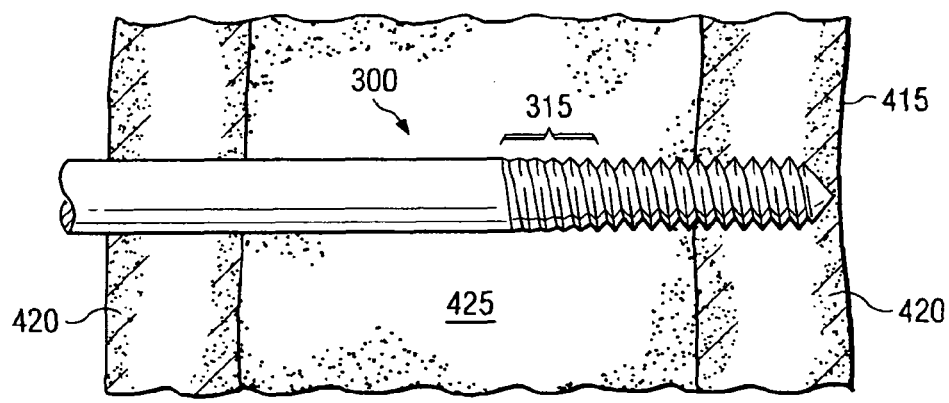
FIG. 4B a cross-section view of bone specimen 415, depicting another exemplary deployment of the fastener 300 of FIGS. 3 and 3A operably secured in cortical bone 420, where thread root transition zone 315 is located inside the bone, in interior region 425.
Figure 4C:
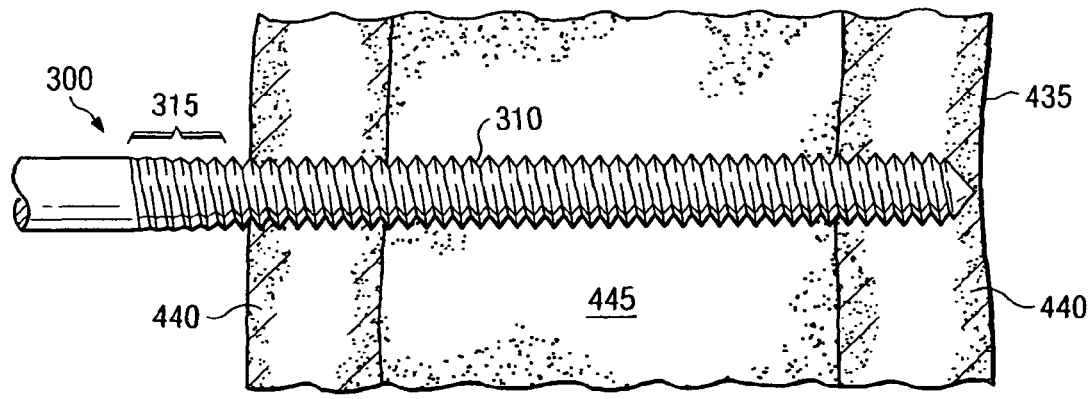
FIG. 4C is a cross-section view of bone specimen 435, depicting another exemplary deployment of the fastener 300 of FIGS. 3 and 3A operably secured in cortical bone 440, where thread root transition zone 315 is located outside the bone (as also illustrated in FIG. 4A), but where threaded portion 310 engages both regions of cortical bone 440 either side of interior region 445.

Turning now to FIGS. 4A, 4B and 4C, exemplary deployments of fastener 300 (as illustrated on FIGS. 3 and 3A) are depicted. In FIGS. 4A, 4B and 4C, fasteners 300 are shown fully secured into specimens of cortical bone. Bone specimen 405 on FIG. 4A, bone specimen 415 on FIG. 4B, and bone specimen 435 on FIG. 4C are shown in cross-section. It will be appreciated that fasteners of the present invention are described and claimed wherein thread root transition zone 315 (as illustrated on FIG. 3A) is located outside of cortical bone when the fastener is operably secured into a specimen of cortical bone. In FIG. 4A, it will be seen that fastener 300 is operably secured into cortical bone 410, and that thread root transition zone 315 is located completely outside of bone specimen 405. By contrast, however, in FIG. 4B, it will be seen that although thread root transition zone 315 is located outside of cortical bone 420, it is still located within bone specimen 415 in which fastener 300 is operably secured. In the exemplary deployment illustrated in FIG. 4B, thread root transition zone 315 is located in interior region 425 of bone specimen 415 It will be appreciated that, depending on the specific bone from which exemplary bone specimen 415 on FIG. 4B may be taken, interior region 425 may comprise cancellous bone and/or fatty bone marrow. FIG. 4C is similar to FIG. 4A in that FIG. 4C shows thread root transition zone 315 is located completely outside of bone specimen 435. However, FIG. 4C shows threaded portion 310 on fastener 300 to be secured into both regions of cortical bone 440 located either side of interior region 445.

It will be further appreciated that orthopedic fasteners according to the present invention are not limited to any particular type of orthopedic application or discipline. For example, without limitation, it is envisaged that orthopedic fasteners according to the present invention will have applications in both human and veterinary orthopedics.

Although the present invention and its advantages have been described in detail, it should be understood that various changes, substitutions and alternations can be made herein without departing from the spirit and scope of the invention as defined by the appended claims.

I claim:

1. A method for securing an orthopedic fastener into cortical bone, the method comprising:
   (a) providing an orthopedic fastener, the orthopedic fastener including:

a cylindrical shank, the cylindrical shank having a preselected diameter, the shank also providing adjacent unthreaded and threaded portions, the threaded portion configured to secure the orthopedic fastener into cortical bone;

the shank further having a thread root transition zone providing a tapered thread root profile between the unthreaded and threaded portions, the tapered thread root profile transitioning from zero to full thread cut over a predetermined number of thread turns; and (b) securing at least a portion of the threaded portion of the orthopedic fastener into a specimen of cortical bone such that, when the orthopedic fastener is operably secured into the specimen of cortical bone, the thread root transition zone is located outside the specimen of cortical bone.

2. The method of claim 1, in which the tapered thread root profile is selected from the group consisting of:
   (a) a conical taper; and
   (b) a curved taper.

3. The method of claim 1, in which the predetermined number of thread turns over which the tapered thread root profile transitions from zero to full thread cut is in a range from about 2 to about 5.

4. The method of claim 1, in which the threaded portion has a substantially uniform thread crest diameter.

5. The method of claim 4, in which the thread crest diameter is substantially the same as the pre-selected diameter of the shank.

6. The method of claim 1, in which the threaded portion has a varying thread crest diameter.

7. The method of claim 1, in which, in step (b), when the orthopedic fastener is operably secured into the specimen of cortical bone, the thread root transition zone is located outside the specimen of cortical bone and at least partially in cancellous bone.

8. The method of claim 1, in which, in step (b), when the orthopedic fastener is operably secured into the specimen of cortical bone, the thread root transition zone is located outside the specimen of cortical bone and not at all in cancellous bone.

9. A method for securing an orthopedic fastener into cortical bone, the method comprising:
   (a) providing an orthopedic fastener, the orthopedic fastener including:
      a cylindrical shank, the cylindrical shank having a preselected diameter, the shank also providing adjacent unthreaded and threaded portions, the threaded portion configured to secure the orthopedic fastener into cortical bone;
      the shank further having a thread root transition zone providing a tapered thread root profile between the unthreaded and threaded portions, the tapered thread root profile transitioning from zero to full thread cut over a predetermined number of thread turns in a range from about 2 to about 5; and
   (b) securing at least a portion of the threaded portion of the orthopedic fastener into a specimen of cortical bone such that, when the orthopedic fastener is operably secured into the specimen of cortical bone, the thread root transition zone is located outside the specimen of cortical bone.

10. The method of claim 9, in which the tapered thread root profile is selected from the group consisting of:
    (c) a conical taper; and
    (d) a curved taper.

11. The method of claim 9, in which the threaded portion has a substantially uniform thread crest diameter.

12. The method of claim 11, in which the thread crest diameter is substantially the same as the pre-selected diameter of the shank.

13. The method of claim 9, in which the threaded portion has a varying thread crest diameter.

14. The method of claim 9, in which, in step (b), when the orthopedic fastener is operably secured into the specimen of cortical bone, the thread root transition zone is located outside the specimen of cortical bone and at least partially in cancellous bone.

15. The method of claim 9, in which, in step (b), when the orthopedic fastener is operably secured into the specimen of cortical bone, the thread root transition zone is located outside the specimen of cortical bone and not at all in cancellous bone.

16. A method for securing an orthopedic fastener into cortical bone, the method comprising:
    (a) providing an orthopedic fastener, the orthopedic fastener including:
       a cylindrical shank, the cylindrical shank having a preselected diameter, the shank also providing adjacent unthreaded and threaded portions, the threaded portion configured to secure the orthopedic fastener into cortical bone;
       the shank further having a thread root transition zone providing a tapered thread root profile between the unthreaded and threaded portions, the tapered thread root profile transitioning from zero to full thread cut over a predetermined number of thread turns in a range from about 2 to about 5; and
    (b) securing at least a portion of the threaded portion of the orthopedic fastener into a specimen of cortical bone such that, when the orthopedic fastener is operably secured into the specimen of cortical bone, the thread root transition zone is located outside the specimen of cortical bone and not at all in cancellous bone.

17. The method of claim 16, in which the tapered thread root profile is selected from the group consisting of:
    (e) a conical taper; and
    (f) a curved taper.

18. The method of claim 16, in which the threaded portion has a substantially uniform thread crest diameter.

19. The method of claim 18, in which the thread crest diameter is substantially the same as the pre-selected diameter of the shank.

20. The method of claim 16, in which the threaded portion has a varying thread crest diameter.

* * * * *